(12) United States Patent
Meyer

(10) Patent No.: US 10,308,540 B2
(45) Date of Patent: Jun. 4, 2019

(54) SYSTEMS AND METHODS FOR PROCESSING ORGANIC COMPOUNDS

(71) Applicant: J.S. Meyer Engineering, P.C., Granite City, IL (US)

(72) Inventor: Stanley Marcus Meyer, Maryville, IL (US)

( * ) Notice: Subject to any disclaimer, the term of this patent is extended or adjusted under 35 U.S.C. 154(b) by 0 days.

(21) Appl. No.: 14/731,420

(22) Filed: Jun. 5, 2015

(65) Prior Publication Data

US 2016/0096761 A1  Apr. 7, 2016

Related U.S. Application Data

(60) Provisional application No. 62/059,236, filed on Oct. 3, 2014.

(51) Int. Cl.
  *C02F 11/04* (2006.01)
  *C02F 3/28* (2006.01)
  (Continued)

(52) U.S. Cl.
  CPC ............ *C02F 11/04* (2013.01); *C02F 3/2806* (2013.01); *C02F 3/286* (2013.01); *C12M 21/04* (2013.01); *C12M 23/58* (2013.01); *C12M 25/18* (2013.01); *C12M 47/18* (2013.01); *C02F 1/722* (2013.01); *C02F 2103/005* (2013.01); *C02F 2103/20* (2013.01); *C02F 2203/00* (2013.01);
  (Continued)

(58) Field of Classification Search
  CPC ............... C02F 11/04; C02F 2103/005; C02F 2103/20; C02F 2203/00; C02F 2303/02; C02F 1/722; C02F 3/2806; C02F 3/286; C02F 2301/08; C02F 2301/106

USPC ........ 210/603, 612, 613, 615, 616, 617, 259
  See application file for complete search history.

(56) References Cited

U.S. PATENT DOCUMENTS 3,388,057 A   6/1968 Callahan
3,966,450 A * 6/1976 O'Neill ................... A61L 11/00
                                                210/759
(Continued)

FOREIGN PATENT DOCUMENTS

CN       201648111 U  * 11/2010
WO       03/035554 A2    5/2003
(Continued)

OTHER PUBLICATIONS

International search report and written opinion of the international searching authority for co-pending PCT application No. PCT/US2015/054076 dated Jan. 20, 2016.
(Continued)

*Primary Examiner* — Fred Prince
(74) *Attorney, Agent, or Firm* — Daniel A. Tallitsch

(57) ABSTRACT

The present disclosure relates to a novel process to control odors from manure by digesting the manure into Methane. Embodiments may comprise a two stage anaerobic digestion process to digest the wastes and remove the nutrients from the wastewater. The initial anaerobic digestion is carried out in a closed vessel to capture any gassed released and otherwise proceeds as current practices are. The wastewater from the first stage digestion is then pumped into a second reaction vessel. This vessel reproduces the conditions that produce natural gas (methane) in the geologic setting, with high temperatures and high pressures.

28 Claims, 1 Drawing Sheet

(51) Int. Cl.

| | | |
|---|---|---|
| *C12M 1/107* | (2006.01) | |
| *C12M 1/00* | (2006.01) | |
| *C12M 1/12* | (2006.01) | |
| C02F 103/00 | (2006.01) | |
| C02F 103/20 | (2006.01) | |
| C02F 1/72 | (2006.01) | |

(52) U.S. Cl.
CPC .... *C02F 2301/08* (2013.01); *C02F 2301/106* (2013.01); *C02F 2303/02* (2013.01)

(56) References Cited

U.S. PATENT DOCUMENTS

| | | | |
|---|---|---|---|
| 4,354,936 A | 10/1982 | Ishida | |
| 4,372,856 A * | 2/1983 | Morrison | C02F 3/28 126/572 |
| 4,604,206 A | 8/1986 | Sullivan | |
| 4,936,996 A * | 6/1990 | Messing | B01D 53/84 210/603 |
| 5,462,666 A * | 10/1995 | Kimmel | C02F 3/04 210/151 |
| 5,630,942 A * | 5/1997 | Steiner | C02F 3/2806 210/603 |
| 5,746,919 A * | 5/1998 | Dague | C02F 3/286 210/603 |
| 6,059,971 A | 5/2000 | Vit | |
| 6,254,776 B1 * | 7/2001 | Seagle | A01K 1/0103 119/447 |
| 6,783,677 B1 * | 8/2004 | Irani | C02F 3/286 210/260 |
| 7,560,026 B2 | 7/2009 | Wilson | |
| 7,906,304 B2 | 3/2011 | Kohr | |
| 8,110,106 B2 | 2/2012 | Allen | |
| 2002/0079266 A1 * | 6/2002 | Ainsworth | C02F 3/28 210/603 |
| 2003/0173291 A1 | 9/2003 | Schimel | |
| 2004/0050777 A1 | 3/2004 | Khan | |
| 2004/0055952 A1 | 3/2004 | Baumgartner | |
| 2005/0145552 A1 | 7/2005 | Sheets | |
| 2009/0255869 A1 | 10/2009 | Oh | |
| 2012/0125840 A1 * | 5/2012 | Smith | C12M 41/48 210/631 |
| 2013/0146533 A1 * | 6/2013 | Arnoldsen, Jr. | C02F 3/284 210/603 |
| 2013/0171710 A1 | 7/2013 | Prebble | |
| 2013/0319940 A1 * | 12/2013 | Josse | C02F 3/286 210/622 |
| 2013/0341269 A1 * | 12/2013 | Bouchet | C02F 3/28 210/631 |
| 2014/0144195 A1 | 5/2014 | Callendrello | |
| 2016/0069220 A1 * | 3/2016 | Wain | F01K 25/08 60/651 |

FOREIGN PATENT DOCUMENTS

| | | |
|---|---|---|
| WO | 2015004146 A1 | 3/2013 |
| WO | 2013033841 A1 | 1/2015 |

OTHER PUBLICATIONS

Patent Disclosure Document filed by Stanley M. Meyer on Oct. 2, 1997.

Roeslein & Associates, Inc. et al. v. Thomas Elgin et al., Complaint, Docket No. 1 (E.D. Mo. Apr. 18, 2017).

Roeslein & Associates, Inc. et al. v. Thomas Elgin et al., The Meyer Defendants' Motion to Dismiss Docket Nos. 45, 46, 46-1, 46-2, 46-3, 46-4, 46-5, 46-6, 46-7 (E.D. Mo. Jul. 31, 2017).

Roeslein & Associates, Inc. et al. v. Thomas Elgin et al., Roeslein's Opposition to the Meyer Defendants' Motion to Dismiss, Docket No. 53 (E.D. Mo. Aug. 21, 2017).

Roeslein & Associates, Inc. et al. v. Thomas Elgin et al., The Meyer Defendants' Reply to Their Motion to Dismiss Docket Nos. 59, 59-1, 59-2, 59-3, 59-4, 59-5, 59-6, 59-7, 59-8 (E.D. Mo. Sep. 11, 2017).

Roeslein & Associates, Inc. et al. v. Thomas Elgin et al., Plaintiffs' Motion for Leave to File Their First Amended Complaint, Docket Nos. 40, 41, 41-1, 41-2 (E.D. Mo. Jul. 31, 2017).

Roeslein & Associates, Inc. et al. v. Thomas Elgin et al., The Meyer Defendants' Opposition to Plaintiffs' Motion for Leave to File Their First Amended Complaint Docket Nos. 54, 54-1, 54-2, 54-3, 54-4, 54-5, 54-6, 54-7, 54-8, 54-9, 54-10, 54-11, 54-12, 54-13, 54-15, 54-16, 54-17, 54-18, 54-19, 54-20, 54-21 (E.D. Mo. Aug. 21, 2017).

Roeslein & Associates, Inc. et al. v. Thomas Elgin et al., Plaintiffs' Reply in Support of their Motion to Amend the Complaint (E.D. Mo. Sep. 11, 2017).

EP Search Report dated Feb. 2, 2018.

Roeslein & Associates, Inc. et al. v. Thomas Elgin et al., Ruling on Motion for Leave to Amend, Docket No. 75 (E.D. Mo. Mar. 2, 2018).

Roeslein & Associates, Inc. et al. v. Thomas Elgin et al., Complaint, Docket No. 76 (E.D. Mo. Mar. 19, 2018).

Letter from Daniel Tallitsch, counsel for J.S. Meyer Engineering P.C., to Michael Nepple, counsel for Roeslein & Associates, Inc., dated Apr. 11, 2018.

Response Letter from Michael Nepple, counsel for Roeslein & Associates, Inc., to Daniel Tallitsch, counsel for J.S. Meyer Engineering P.C., dated Apr. 23, 2018.

Transcript of Evidentiary Hearing Before the Honorable John M. Bodenhausen held on Oct. 3, 2018 in St. Louis, Missouri, in the case of Roeslein & Associates, Inc. v. Elgin, No. 4:17-cv-1351 (JMB) pending in the United States District Court for the Eastern District of Missouri, (2018).

Zhang, R.H. et al, "Evaluation of Two Stage Anaerobic Sequencing Batch Reactor Systems for Animal Wastewater Treatment," Transactions of the ASAE, vol. 43(6):1795-1801, 2000.

* cited by examiner

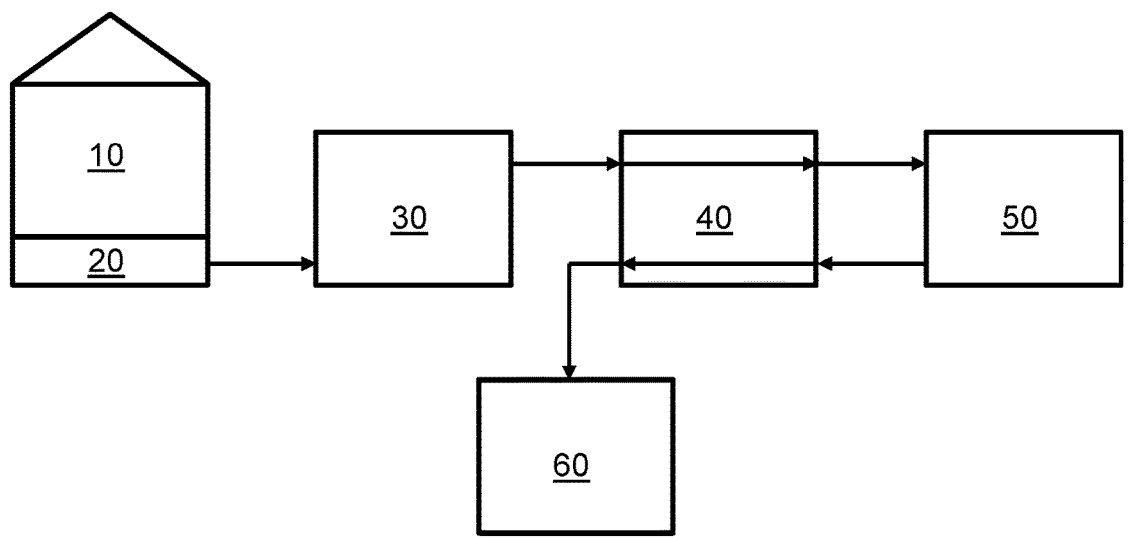

SYSTEMS AND METHODS FOR PROCESSING ORGANIC COMPOUNDS

CROSS-REFERENCE TO RELATED APPLICATIONS

This application claims priority to U.S. Provisional Application No. 62/059,236 filed Oct. 3, 2014, the contents of which are hereby incorporated in its entirety by reference.

FIELD OF THE DISCLOSURE

The present disclosure relates to a novel process to control odors from manure by digesting the manure into Methane.

BACKGROUND OF THE DISCLOSURE

Current waste management processes for manure from medium to large animal husbandry operations fall into three basic types. Small and some medium size confinement operations apply the produced effluent as fertilizer, often causing odor complaints. Aerobic digestion of the waste requires that the waste be liquefied, and air be bubbled through the waste water to sustain oxygen using bacteria as they break down the solid and liquid wastes. Anaerobic digestion of the waste occurs when bacteria that do not use oxygen dominate the process. This occurs rapidly if the air injection system fails in the aerobic digester, or by design in an anaerobic lagoon, or naturally if the waste is allowed to accumulate untreated. Anaerobic digestion includes bacteria that use sulfur and release hydrogen sulfides, which are the compounds that cause odor complaints.

SUMMARY

The proposed process uses a two stage anaerobic digestion process to digest the wastes and remove the nutrients from the wastewater. The initial anaerobic digestion is carried out in a closed vessel to capture any gasses released and otherwise proceeds as current practices are. The wastewater from the first stage digestion is then pumped into a second reaction vessel. This vessel reproduces the conditions that produce natural gas (methane) in the geologic setting, with high temperatures and high pressures.

The proposed process works by converting the carbon nutrients in the wastewater into methane, using bacteria that flourish in the conditions that exist at the geologic depth of 1000 feet or more below the ground surface. The second stage reactor has a large surface area from porous rock to provide a substrate for the bacteria to grow on. The reactor is pressurized and heated to reproduce the conditions that the desired bacteria thrive in. These bacteria also remove much of the nutrients from the wastewater and lower the biological oxygen demand by an order of magnitude of greater.

The initial stage produces both methane and sulfides. This process provides for control of both these gasses. The sulfides are absorbed in a chemical scrubber, by any of various well known techniques such as passing the gas through a bed of finely divided iron oxide. The methane is collected and can be used to produce some of the energy required to pressurize and heat the second stage reactor. This pressurization and heating destroys all the bacteria from the first stage except desired varieties that thrive deep underground. Some of the methane produced by the second stage reactor can also be used to produce the energy to achieve the necessary conditions in the second stage reactor. The balance of the total quantity of methane produced from both stages is available for other uses.

BRIEF DESCRIPTION OF THE DRAWINGS

Some embodiments of the disclosure may be understood by referring, in part, to the present disclosure and the accompanying drawings, wherein:

FIG. 1 illustrates an example system according to a specific example embodiment of the present disclosure.

DETAILED DESCRIPTION

The waste from animal confinement area 10 is sluiced into a holding pit 20. The waste is then pumped into the initial stage 30 where the biological reaction takes place over a space of several hours. Any gasses formed are removed from the vessel. The resulting liquid is then removed from the first vessel 30 and pumped at pressure through a heat exchanger 40 where it is heated, and into the second vessel 50. This second vessel 50 contains a porous material such as lava rock that acts as substrate for bacteria. The liquid passes over and through the substrate and is contained in the reactor 50 for a period of time. It is then discharged and pumped through the heat exchanger 40 counter current to the feed stream to the reactor 50, thus, cooling the product and heating the feed.

Once the stream is discharged from the heat exchanger the pressure is reduced and the resulting gasses collected. Sulfides are removed and the gas is stored. Energy to operate the compressor, and provide any required supplemental heating can be provided by combustion of the stored methane. If necessary, the final liquid can be passed through an oxygenation system 60 such as bubbler or spray arrangement to re-oxygenate the water and further reduce the biological oxygen demand to meet environmental standards for discharge. Periodically solids are removed from both reactor vessels 30, 50 and applied as fertilizer to the land. The material either liquid or solid has had the temperature raised above the sterilization temperature to produce a more land friendly applicant.

The water from this operation is recycled, or fresh water can be used, to clean the confinement/feed lot operation. Odor in the confinement operation is controlled by periodic cleaning of the facility. An oxidizer not limited to or combinations of potassium permanganate, sodium permanganate or hydrogen peroxide is added to the wash water to retard the formation of septic wastes prior to their introduction into the digester system. This prevents the growth of odor causing bacteria and reduces the overall odor of the operation.

This invention has further application in that it may be applied to any organic waste treatment process and can replace or supplement treatment of human waste as well as animal manure. Some organic chemical wastes may also be treatable by this process.

The following embodiments are contemplated:

1. The production of methane in an enclosed biological reactor system with controlled temperature and pressure using bacteria, that flourish at elevated temperatures and pressures as a waste treatment process.

2. A two stage process where the first stage 30 is at a lower pressure and temperature than the second 50. The first stage 30 separates the solids from the liquids via gravity separation. The process also covers certain embodiments where a mechanical device can be incorporated into the system to separate the solids.

3. A two stage process where the second stage 50 is at a pressure and temperature elevated to increase the reaction rate.

4. A two stage process where the effluent from the second stage 50 is recycled back to the first stage so the heat can be exchanged between the two stages.

5. A two stage process where the recycle fluid is used to agitate the first stage 30 so that the reaction rate of the first step is improved.

6. A two stage process where the temperature of the second phase exceeds sterilization temperature producing a material more suitable for land application.

7. The control of odors from waste treatment through the production of methane in an enclosed biological reactor system with controlled temperature and pressure.

8. The recovery of energy by the production of methane from waste treatment in an enclosed biological reactor system with controlled temperature and pressure.

9. The use/application of potassium permanganate, sodium permanganate, or hydrogen peroxide as an oxidizer in the animal confinement area 10 to prevent the growth of odor causing bacteria.

10. The use/application of potassium permanganate, sodium permanganate, or hydrogen peroxide as an oxidizer in the animal confinement area 10 to destroy sulfur compounds causing odors.

11. The recycling of treated water clean waste from the animal confinement area 10, minimizing discharge of produced water.

12. Concentration of the produced effluent via ion exchange or evaporation to produce a liquid fertilizer 13. Removal of the methane producing organics in the effluent reducing the discharge of methane from the land applied material and subsequent reduction of the carbon dioxide footprint.

The title, abstract, background, and headings are provided in compliance with regulations and/or for the convenience of the reader. They include no admissions as to the scope and content of prior art and no limitations applicable to all disclosed embodiments.

What is claimed is:

1. A system for processing a material comprising one or more organic compounds, the system comprising:
   a first anaerobic chamber, wherein the first anaerobic chamber is configured to receive the organic compounds, and wherein the first anaerobic chamber is configured to process the organic compounds and provide a first fluid stream;
   a heat exchanger configured to receive the first fluid stream from the first anaerobic chamber and a second fluid stream from a second anaerobic chamber, wherein the heat exchanger is configured to transfer heat from the second fluid stream to the first fluid stream, whereby the first fluid stream exiting the heat exchanger is a heated fluid stream and whereby the second fluid stream exiting the heat exchanger is a cooled fluid stream;
   the second anaerobic chamber being configured to receive the heated fluid stream provided by the heat exchanger, wherein the heated fluid stream leaving the second anaerobic chamber is the second fluid stream;
   a heater for heating the heated fluid stream received by the second anaerobic chamber; and,
   wherein the first anaerobic chamber is configured to be operated at a lower temperature than the second anaerobic chamber.

2. The system of claim 1 further comprising a first containment chamber that provides the organic compounds to the first anaerobic chamber, wherein the first containment chamber comprises at least a portion of an animal confinement area.

3. The system of claim 1, wherein the material comprises animal manure.

4. The system of claim 1, wherein the second anaerobic chamber further comprises a substrate with bacteria growing thereon.

5. The system of claim 4, wherein the substrate comprises lava rock.

6. The system of claim 1, wherein the first anaerobic chamber is configured to be operated at a lower pressure than the second anaerobic chamber.

7. The system of claim 1 further comprising an oxygenation system, wherein the oxygenation system receives the cooled fluid stream, wherein an oxidizer is disposed in the oxygenation system.

8. The system of claim 1 further comprising a sulfide gas treating unit, wherein the sulfide gas treating unit is in fluid communication with the second anaerobic chamber.

9. The system of claim 1, wherein the system comprises no additional anaerobic chambers other than the first anaerobic chamber and the second anaerobic chamber.

10. The system of claim 1, wherein the first anaerobic chamber is configured to generate a liquid wastewater stream from the organic compounds, and wherein the first fluid stream consists of the liquid wastewater stream, whereby only the first fluid stream is provided from the first anaerobic chamber to the heat exchanger.

11. A method for processing a material comprising one or more organic compounds, the method comprising:
   receiving at a first anaerobic chamber the organic compounds,
   treating in the first anaerobic chamber the organic compounds;
   providing from the first anaerobic chamber a first fluid stream;
   receiving from a heat exchanger a heated fluid stream at a second anaerobic chamber;
   treating in the second anaerobic chamber the heated fluid stream, wherein the first anaerobic chamber is configured to be operated at a lower temperature than the second anaerobic chamber;
   providing from the second anaerobic chamber a second fluid stream;
   receiving at the heat exchanger the first fluid stream and the second stream;
   transferring heat from the second fluid stream to the first fluid stream at the heat exchanger;
   providing the first fluid stream from the heat exchanger as the heated fluid stream; and,
   providing the second fluid stream from the heat exchanger as a cooled fluid stream.

12. The method of claim 11 further comprising a first containment chamber that supplies the organic compounds for the first anaerobic chamber, wherein the first containment chamber comprises at least a portion of an animal confinement area.

13. The method of claim 11, wherein the material comprise animal manure.

14. The method of claim 11, wherein the second anaerobic chamber further comprises a substrate with bacteria growing thereon.

15. The method of claim 14, wherein the substrate comprises lava rock, and wherein the heated fluid stream is passed over the lava rock.

16. The method of claim 11, wherein the first anaerobic chamber is configured to be operated at a lower pressure than the second anaerobic chamber.

17. The method of claim 11 further comprising an oxygenation system, wherein an oxidizer is disposed in the oxygenation system, wherein the method further comprises receiving from the heat exchanger the cooled fluid stream at the oxygenation system.

18. The method of claim 11, wherein the method further comprises receiving, from the second anaerobic chamber, sulfide gases at a sulfide gas treating unit.

19. The method of claim 11, wherein the method that treats the organic compounds comprises no additional anaerobic chambers other than the first anaerobic chamber and the second anaerobic chamber.

20. The method of claim 11, wherein the first anaerobic chamber is configured to generate a liquid wastewater stream from the organic compounds, wherein the first fluid stream consists of the liquid wastewater stream, whereby only the first fluid stream is provided from the first anaerobic chamber to the heat exchanger.

21. A system for processing a material comprising one or more organic compounds, the system comprising:
- a first anaerobic chamber, wherein the first anaerobic chamber is configured to receive the organic compounds, and wherein the first anaerobic chamber is configured to process the organic compounds and generate a liquid wastewater stream from the organic compounds;
- a second anaerobic chamber, wherein the second anaerobic chamber is configured to receive the liquid wastewater stream provided by the first anaerobic chamber, wherein the first anaerobic chamber is configured to be operated at a lower temperature and at a lower pressure than the second anaerobic chamber.

22. The system of claim 21 further comprising a first containment chamber that provides the organic compounds to the first anaerobic chamber, wherein the first containment chamber comprises at least a portion of an animal confinement area.

23. The system of claim 21, wherein the material comprises animal manure.

24. The system of claim 21, wherein the second anaerobic chamber further comprises a substrate with bacteria growing thereon.

25. The system of claim 24, wherein the substrate comprises lava rock.

26. The system of claim 21 further comprising a sulfide gas treating unit, wherein the sulfide gas treating unit is in fluid communication with the second anaerobic chamber.

27. The system of claim 21, wherein the system comprises no additional anaerobic chambers other than the first anaerobic chamber and the second anaerobic chamber.

28. A system for processing a material comprising one or more organic compounds, the system comprising:
- a first anaerobic chamber, wherein the first anaerobic chamber is configured to receive the organic compounds, and wherein the first anaerobic chamber is configured to process the organic compounds and generate a liquid wastewater stream from the organic compounds;
- a second anaerobic chamber, wherein the second anaerobic chamber is configured to receive the liquid wastewater stream provided by the first anaerobic chamber, wherein the first anaerobic chamber is configured to be operated at a lower temperature than the second anaerobic chamber; and,
- an oxygenation system, wherein the oxygenation system receives a fluid stream leaving the second anaerobic chamber, wherein an oxidizer is disposed in the oxygenation system.

* * * * *